(12) United States Patent
Knoll

(10) Patent No.: US 6,287,438 B1
(45) Date of Patent: Sep. 11, 2001

(54) SAMPLING SYSTEM FOR ANALYTES WHICH ARE FLUID OR IN FLUIDS AND PROCESS FOR ITS PRODUCTION

(76) Inventor: Meinhard Knoll, Geschwister-Scholl-Stasse 9, D-48565 Steinfurt (DE)

(*) Notice: Subject to any disclaimer, the term of this patent is extended or adjusted under 35 U.S.C. 154(b) by 0 days.

(21) Appl. No.: 09/117,077
(22) PCT Filed: Jan. 28, 1997
(86) PCT No.: PCT/DE97/00192
§ 371 Date: Sep. 23, 1998
§ 102(e) Date: Sep. 23, 1998
(87) PCT Pub. No.: WO97/27475
PCT Pub. Date: Jul. 31, 1997

(30) Foreign Application Priority Data

Jan. 28, 1996 (DE) .............................................. 196 02 861

(51) Int. Cl.$^7$ .................................................. G01N 27/26
(52) U.S. Cl. ........................ 204/409; 204/403; 204/418; 204/419
(58) Field of Search ................................. 204/403, 409, 204/415, 418, 419

(56) References Cited

FOREIGN PATENT DOCUMENTS

579997 A1 * 1/1994 (EP) .

* cited by examiner

Primary Examiner—T. Tung
Assistant Examiner—Alex Noguerola
(74) Attorney, Agent, or Firm—Marshall & Melhorn, LLC

(57) ABSTRACT

The invention concerns a sampling system and a process for its production. Such systems can easily be employed throughout in chemical and biochemical analysis. The sampling system should be simply constructed and universally usable alone and in combination and fabricable with little effort. The sampling system constructed as per the invention for analytes which are fluid or are contained in fluids consists of a planar support with various holes in it through which the particular fluid can pass into a channel which it subsequently exits. The channel is at least partly covered by a cover over the side opposite the support. In addition, a membrane pervious to the analyte is inserted which at least partly covers the channel on its open upper side. The areas not covered by the cover can be used to extract the analyte or to make direct measurements.

35 Claims, 22 Drawing Sheets

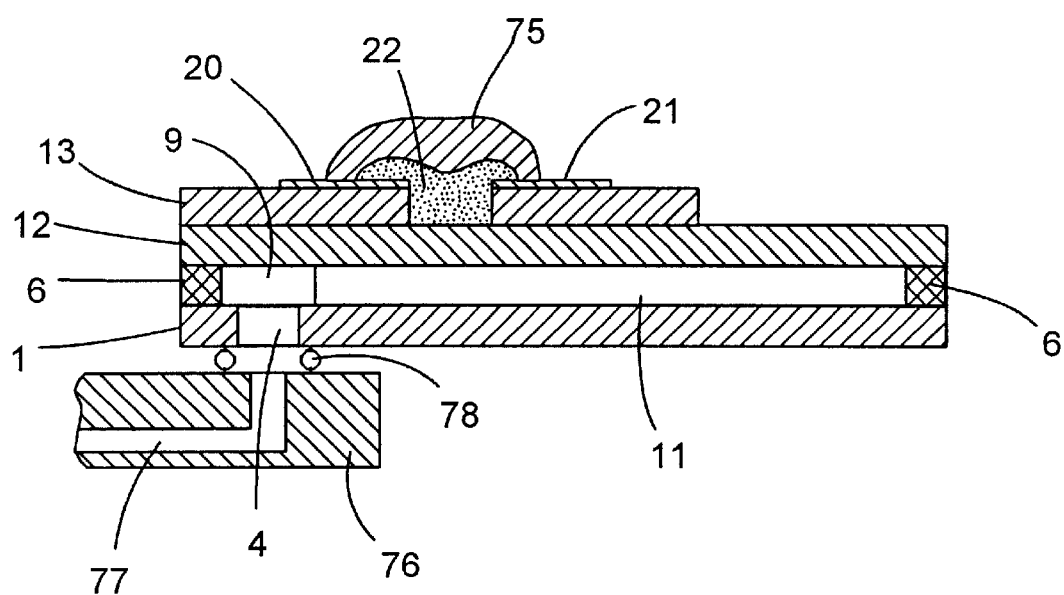
F I G. 20

SAMPLING SYSTEM FOR ANALYTES WHICH ARE FLUID OR IN FLUIDS AND PROCESS FOR ITS PRODUCTION

BACKGROUND OF THE INVENTION

1. Field of the Invention

The invention relates to a sampling system and to a process for its production. Systems of this type can be used simply and universally in chemical and biochemical analysis.

2. Description of Prior Art

It is known that electrochemical sensors are used to determine concentrations of substances in liquids (cf. F. Oehme: Chemische Sensoren [Chemical sensors], Vieweg Verlag, Braunschweig, 1991).

Besides individual sensors, it is also possible, with the aid of semiconductor technology, to produce continuous-flow analysis systems with integrated sensor elements (DE 44 08 352).

Continuous-flow systems of this type have the particular advantage that not only the liquid medium to be measured, but also calibration liquids can be pumped alternately through the system, so that regular calibration of the sensors is possible.

It is also known that continuous-flow analysis systems of this type can be equipped with a simple sampling device—a microdialysis needle.

Furthermore, a particularly cost-efficient mass-production technique has been introduced for the production of individual sensors (DE 41 15 414).

A disadvantage with the prior art is that continuous-flow analysis systems using silicon technology can be produced with low costs per item only if the number of items needed exceeds 100,000 per year. The same is true as regards microdialysis needles, which at the present time are still produced using skilled labour techniques.

Furthermore, the connection technique for continuous-flow sensors and microdialysis needles has not been developed to an extent such that tube and channel connections for the liquid medium to be measured can be produced, without cross-sectional widening and dead volume, with tolerable outlay.

SUMMARY OF THE INVENTION

The object of this invention is therefore to provide a sampling system which is of simple design, universally usable on its own and in combination and produceable at low cost.

This object is achieved according to the invention with the features of Claim 1 for the sampling system, and with the features of Claim 31 for the production process.

The sampling system formed according to the invention for fluid analytes or analytes contained in fluids is made of a flat support, into which various holes are introduced through which the relevant fluid can enter a channel and then leave it again. The channel is covered at least partly by a cover on the opposite side from the support. Furthermore, use is made of a membrane which is permeable to the analyte and at least partly covers the channel on the open upper side of the latter. The regions left free by the cover can be used to take up the analyte or for direct measurement there.

This being the case, there is the possibility of arranging a separate channel support between the support proper and the membrane with the cover on top. The channel may, however, also be formed directly in the support.

If a channel support is used, it is favourable to provide it with additional holes which, when the sampling system formed according to the invention has been assembled, correspond to the abovementioned holes in the support.

The sampling system formed according to the invention is of very simple design and can be used universally for a variety of measurement tasks. There is thus the possibility, on the one hand, of taking the sample, separating the analyte to be determined from the carrier fluid, and taking it for subsequent analysis.

The sampling system may, however, also be used in direct combination with sensor elements, and for example concentrations of substances in a particular analyte can be taken directly from the sampling system.

In this case, the simple design, in particular, and consequently the very cost-effective production are advantageous.

Very simple and accurate measurements can thus be taken with the sampling system according to the invention, when use is made of correspondingly formed sensor elements, together with corresponding reference electrodes.

Furthermore, calibrations can be made in simple and favourable fashion.

An example of a sample system formed according to the invention may be designed such that a support 1 having at least two holes 4, 5 is firmly connected to a channel support 6 having at least two holes 9, 10 and at least one channel 11, and the channel support 6 is firmly connected to at least one membrane 12 and the membrane 12 is firmly connected to a cover 13, and the channel 11 can be supplied through the holes 4, 5 as well as 9, 10 with the analyte or a carrier liquid or carrier gas which contains it and flows through this channel and can pick up the analyte which is in contact with the membrane 12, which is permeable to this analyte, in the uncovered region 14 of the membrane 12, and the analyte, or alternatively the carrier liquid containing it, can flow through the channel past the openings 16, 17 which are located in the cover 13 and into which it is possible to place electrochemical or optical sensor elements with which concentrations of substances or ion activities can be measured.

The support 1 and the channel support 6 are made of a material which is inert with respect to the analyte and the carrier fluid, for example of plastic (polyvinyl chloride (PVC), polyethylene (PE), polyoxymethylene (POM), polycarbonate (PC), ethylene/propylene copolymer (EPDM), polyvinylidene chloride (PVDC), polychlorotrifluoroethylene, polyvinyl butyral (PVB), cellulose acetate (CA), polypropylene (PP), polymethyl methacrylate (PMMA), polyamide (PA), tetrafluoroethylene/hexafluoropropylene copolymer (FEP), polytetrafluoroethylene (PTFE), phenol formaldehyde (PF), epoxide (EP), polyurethane (PUR), polyester (UP), silicone, melamine formaldehyde (MF), urea formaldehyde (UF), aniline formaldehyde, capton etc.).

The support 1 may, for example, also be manufactured from glass, ceramic or silicon. The same is true as regards the channel support 6.

The holes 4, 5 and 9, 10 in the support 1 and in the channel support 6 as well as the channel 11 are produced in such a way that the support 1 and/or the channel support 6 are created by injection-moulding or compression techniques or the LIGA method with these structures, or these structures are subsequently produced by cutting, stamping, milling, boring, etching, laser cutting or electric discharge machining or the like.

The typical dimensions of the support 1 are for its length, from 1 to 10 cm, for its width from 0.5 to 5 cm, and for its thickness from 0.1 to 1 mm. The same or similar values apply to the channel support 6. The holes 4, 5 and 9, 10 have diameters of between 0.1 and 10 mm. The width of the channel 11 is between 0.1 and 10 mm.

The solid connection between the support 1 and the channel support 6 may, depending on the material, be made according to the prior art by adhesive bonding, welding or laminating (in the case of plastics) or adhesive bonding (in the case of glass, ceramic, silicon) or anodic bonding (in the case of glass on silicon).

For the lamination of plastic sheets, special laminating sheets are also available on the market, which can be hot-laminated (for example CODOR sheet made of polyethylene and polyester from the company TEAM CODOR, Deutschland, Marl).

The membrane 12 is, depending on the application, formed as a dialysis membrane, gas-permeable membrane, lattice or fabric of plastic fibres, paper fibres or textile fibres. Its thickness is between 10 and 1000 $\mu$m. The following materials can be used for dialysis membranes: polycarbonate, cellulose acetate, cellulose hydrate, cuprophane, thomapor, regenerated cellulose, polyacrylonitrile, polysulphone, polyamide and polymethyl methacrylate etc.

The following materials can be used for a gas-permeable membrane: polyvinyl chloride (PVC), polyethylene (PE), polyoxymethylene (POM), polycarbonate (PC), ethylene/propylene copolymer (EPDM), polyvinylidene chloride (PVDC), polychlorotrifluoroethylene, polyvinyl butyral (PVB), cellulose acetate (CA), polypropylene (PP), polymethyl methacrylate (PMMA), polyamide (PA), tetrafluoroethylene/hexafluoropropylene copolymer (FEP), polytetrafluoroethylene (PTFE), phenol formaldehyde (PF), epoxide (EP), polyurethane (PUR), polyester (UP), silicone, melamine formaldehyde (MF), urea formaldehyde (UF), aniline formaldehyde and capton etc.

Besides the choice of material, the thickness of the membrane is also a dominant factor for the gas permeability.

The solid connection between the membrane 12 and the channel support 6 may, according to the prior art, be made by adhesive bonding, welding or laminating.

The cover 13 is produced using a process which is the same as or similar to that for the support 1, and is firmly connected by adhesive bonding, welding or laminating to the membrane such that the latter, is fully or partly covered by the cover 13.

Into the openings 16, 17 in the cover 13, it is possible to integrate any sensor elements which can be made small enough, and for example are known from F. Oehme: Chemische Sensoren, Vieweg Verlag, Braunschweig, 1991 or from DE 41 15 414.

The particular advantages of this invention reside in the fact that chemical and biochemical sensors can be produced in multi-sensor arrangements together with continuous-flow channels as well as microdialysis elements as a unit such that they can be produced at low cost. It is therefore possible, with one device, to take up the sample and measure concentrations of substances with the aid of integrated sensors. The continuous-flow arrangement makes it possible for the sensors to be calibrated regularly with the aid of calibration liquids. If the channel cross-section is small, the system can be used according to the microdialysis principle on account of the capillary constriction effect.

Furthermore, it is not necessary to have increases in cross-section between the site where the sample is taken up in the region 14 of the uncovered membrane surface and the sites at which sensor elements in the openings 16, 17 in the cover 13 are in contact with the carrier liquid.

Furthermore, it is therefore very readily possible to integrate sensor elements into the continuous-flow system since, before the sensor element has been introduced, the channel is already covered with a membrane 12 which is permeable to the analyte, and this also makes it possible to introduce additional membrane solutions without them flowing into the channel underneath.

BRIEF DESCRIPTION OF THE DRAWING

Illustrative embodiments of the invention are represented in FIGS. 1 to 22, in which:

FIG. 20 shows a sampling system according to FIG. 4 with a connection block;

DESCRIPTION OF THE PREFERRED EMBODIMENT

Figure 1:
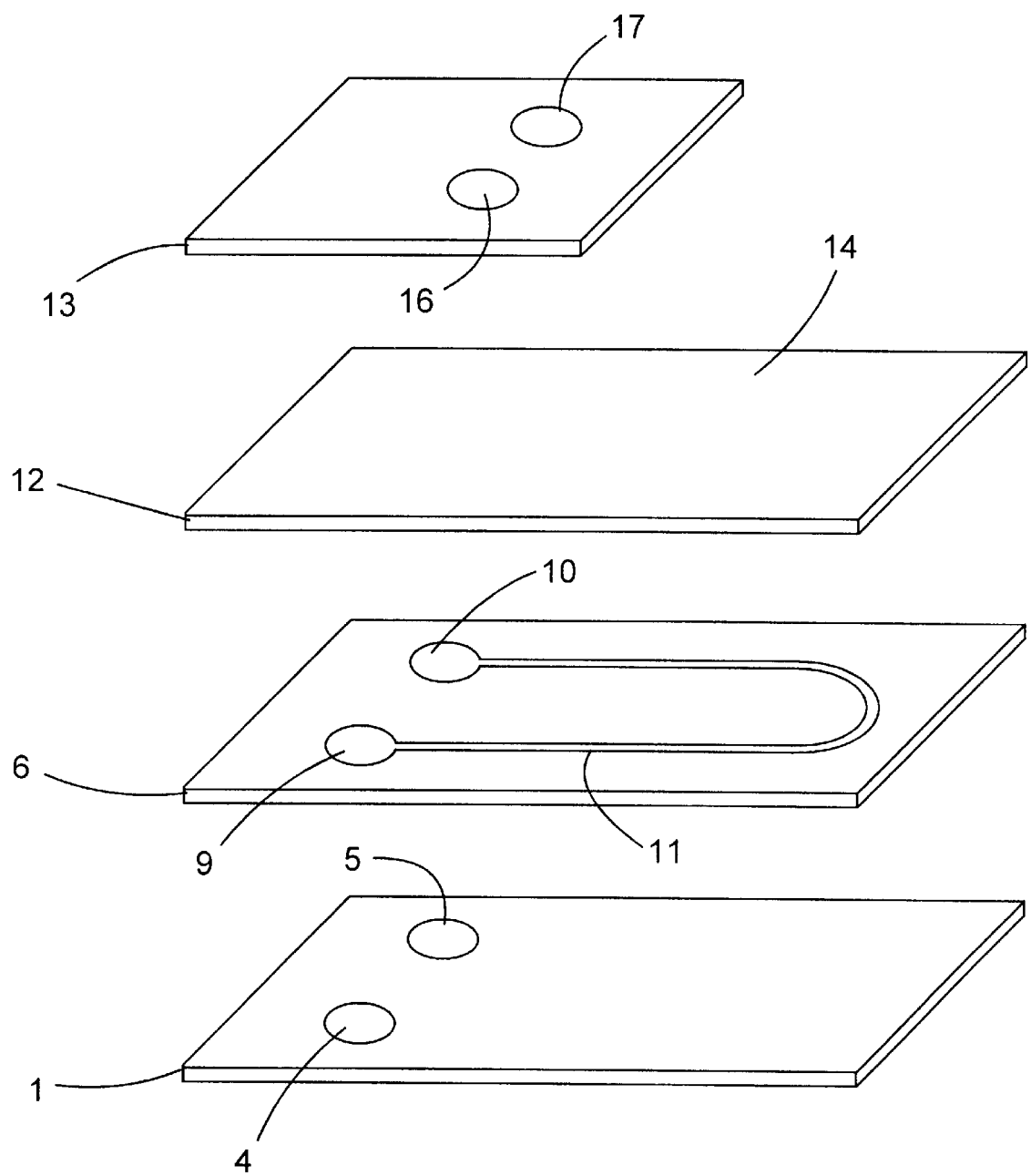
FIG. 1 shows a layer structure of a first example of a sampling system, into which sensor elements can be integrated.
Figure 2:
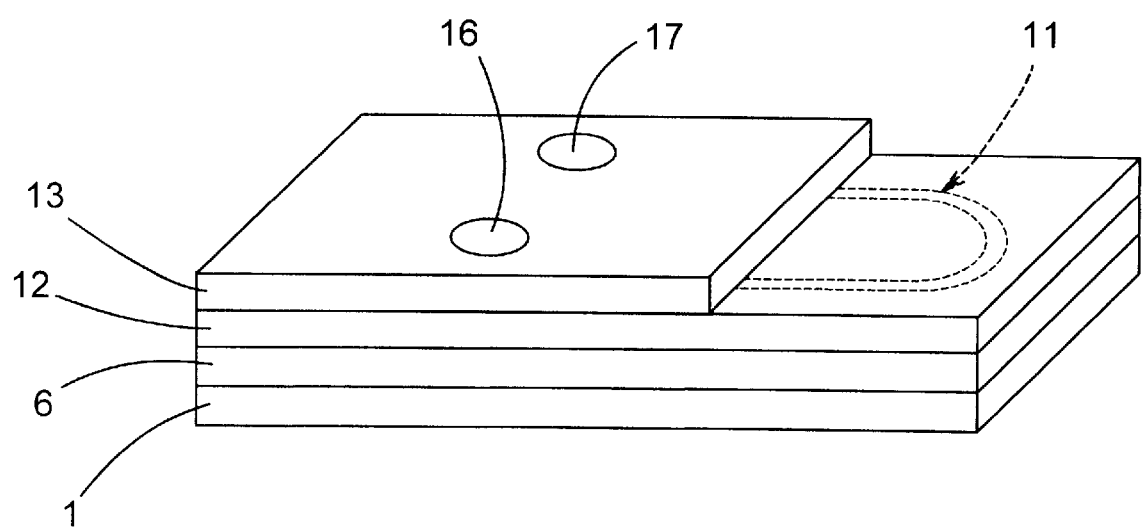
FIG. 2 shows a sampling system according to FIG. 1.
Figure 3:
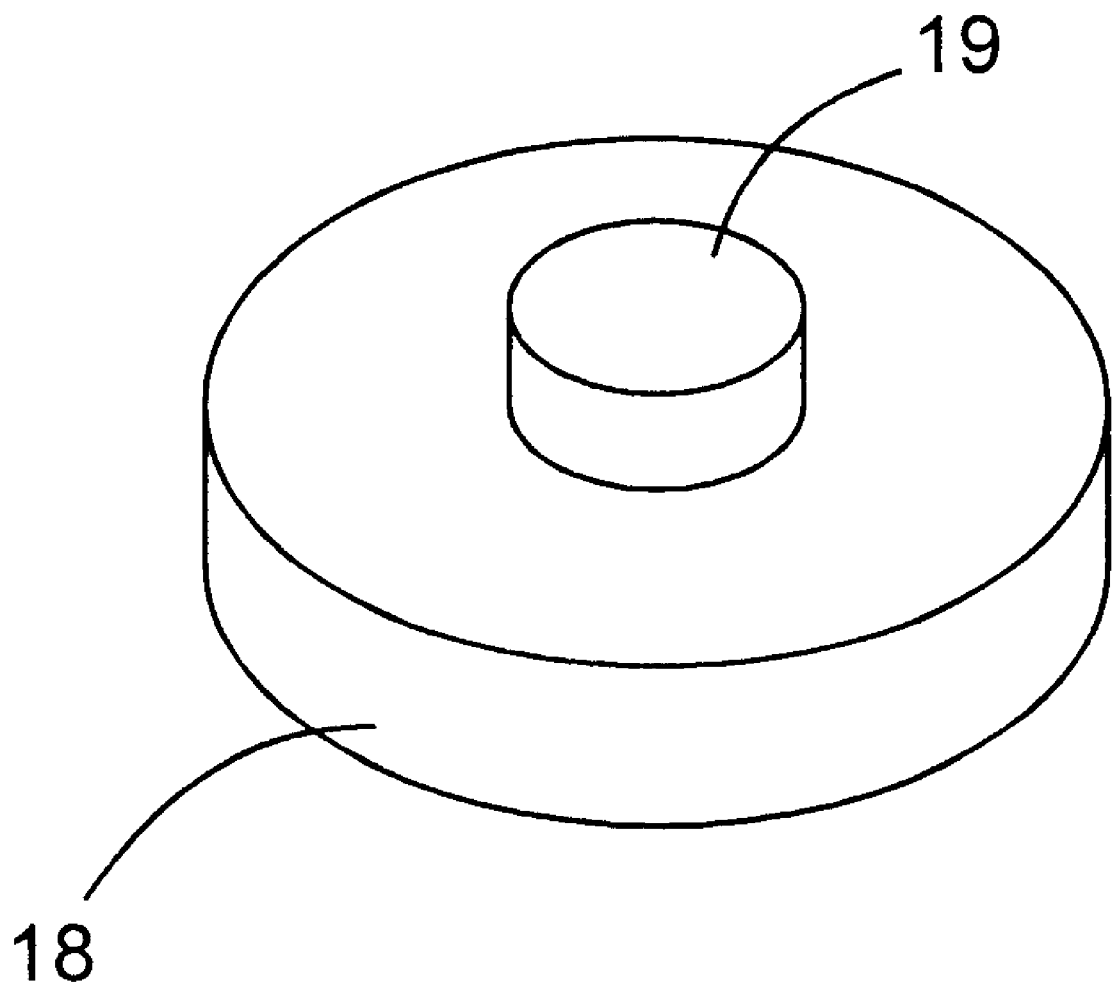
FIG. 3 shows a sensor element of a sampling system which can be integrated into holes.

A first illustrative embodiment is represented in FIGS. 1 to 3. FIG. 1 shows the layer sequence of a sampling unit into which sensor elements can be integrated. FIG. 2 represents the layer structure after the various planes have been assembled and have been firmly connected. Sensor elements, as for example disclosed by DE 41 15 414, can be integrated into the openings 16, 17 in the cover 13. A sensor element of this type is shown in FIG. 3. In this figure, an ion-selective membrane 18 is in direct contact with a silver noble-metal lead 19. This sensor element is inserted into the opening 16 in the cover 13 in such a way that the ion-selective membrane 18 is in direct contact with the membrane 12, and a contact pin can make contact with the noble-metal lead 19 through the opening 16, and this lead can be connected to measuring electronics. The sensor element according to FIG. 3 may then additionally be fixed to the surface of the cover 13 using an adhesive, in such a way that the noble-metal lead remains free of adhesive. In order to improve the electrochemical contact between the membrane 12 and the ion-selective membrane 18, the membrane 12 in the opening 16 may be coated with a thin hydrogel film (for example HEMA) before the sensor element is inserted, this film being introduced into the opening (16) in the form of a solution, and the sensor element according to FIG. 3 is inserted after the hydrogel film has been formed.

A reference electrode, constructed in the same way as the sensor element according to FIG. 3, is inserted into the opening 17. In this case, however, the layer 18 in FIG. 3 is made of a KCl gel and the layer 19 is made of a chloridized silver film.

In this example, the support 1, the channel support 6 and the cover 13 are made of a 150 μm thick laminating sheet by stamping. This sheet is made of polyethylene and polyester and is commercially available under the name CODOR sheet. The membrane 12 is a 20 to 100 μm, preferably 50 μm thick polycarbonate dialysis membrane. The solid connection of the support 1, the channel support 6, the membrane 12 and the cover 13 is made by laminating at 125° C.

In order to take a measurement, a carrier liquid (for example a sodium chloride solution) is pumped through the hole 5 in the support into the channel region 11. The carrier liquid leaves the arrangement through the hole 4 in the carrier 1. The surface 14 of the membrane 12 not covered by the cover 13 is, for example by immersion, brought into direct contact with the liquid.medium to be measured, and the analyte can be taken up there.

The ions involved in the measurement diffuse through the dialysis membrane 12, enter the carrier-liquid flow in the channel 11, and are transported to the sensor element located in the opening 16 in the cover 13. The ion-selective membrane 18 of the sensor element according to FIG. 3 is therefore in contact with the medium to be measured, via the dialysis membrane. Depending on the activity of the ion involved in the measurement, a potential difference is formed between the solution to be measured and the ionselective membrane, and this potential difference can be measured between the metal leads 19 of the sensor element or of the reference electrode with the aid of a high-impedance millivoltmeter.

It is, however, also possible to insert known optical sensor elements instead of electrochemical sensor elements into the openings 16, 17.

Figure 4:
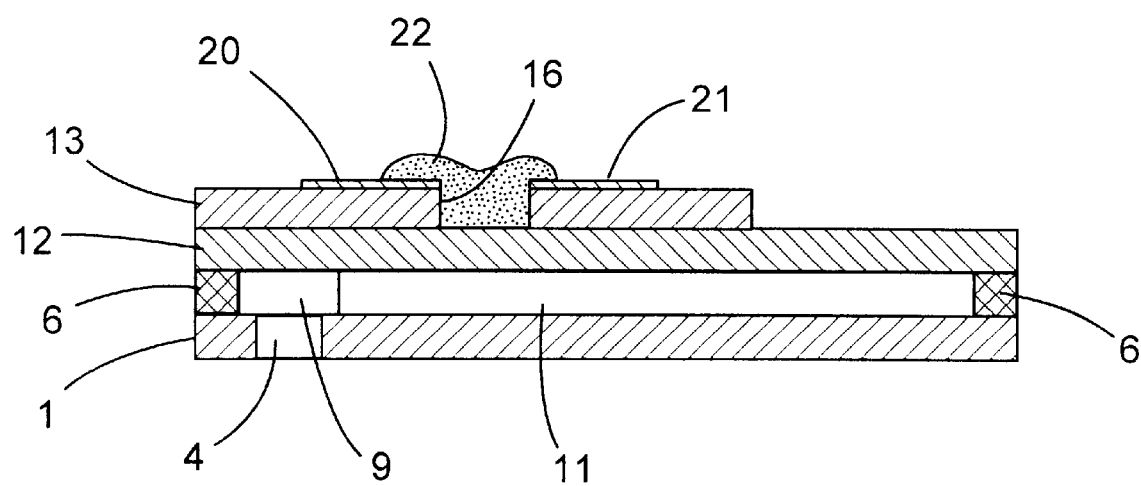
FIG. 4 shows a second illustrative embodiment of a sampling system with an ion-selective sensor element.

A second illustrative embodiment is represented in FIG. 4. FIG. 4 shows an arrangement according to FIG. 1 and FIG. 2 in section. Unlike in FIGS. 1 and 2, a sensor element according to FIG. 3 is not in this case inserted into the opening 16 in the cover 13. Here, in FIG. 4, a 0.1 to 1 μm thick noble-metal film 20, 21 (for example made of silver) is applied in order to produce a sensor element to the cover 13 with the aid of the evaporation, sputtering or screen printing techniques (both noble-metal films 20, 21 are made of the same material and are connected to one another). Next, with the aid of a micropipette or an automatic dispenser, a membrane solution, for example made of PVC or silicone with ion carriers, is introduced into the opening 16. Membrane solutions of this type are, amongst others, also known from F. Oehme, Chemische Sensoren, Vieweg Verlag, Braunschweig, 1991. After the sensor membrane 22 has been solidified by evaporating the solvent or by cross-linking under UV light, this arrangement acts as an ion-selective sensor element. A similar element may be introduced as a reference electrode in the opening 17. In this case, the membrane 22 is designed as a KCl gel and the metal film 20, 21 is designed as a silver film whose surface is chloridized.

Figure 5:
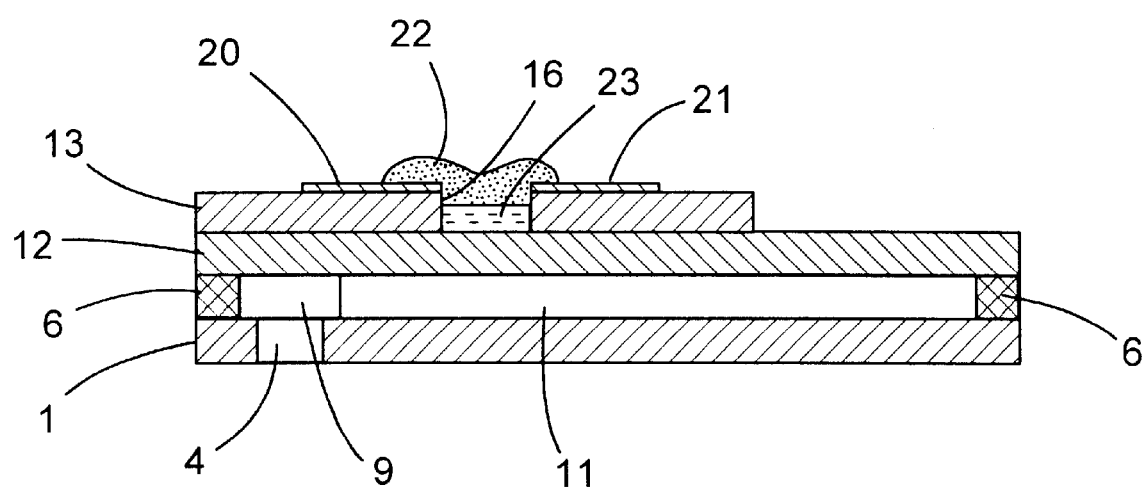
FIG. 5 shows a third illustrative embodiment of a sampling system with a biosensor element.

A third illustrative embodiment is shown by FIG. 5. This representation corresponds to the representation in FIG. 4. However, an additional membrane 23 is introduced in this case. If this membrane 23 is designed as a gel layer with an enzyme (for example the enzyme urease) and the membrane 22 is designed as a pH-sensitive or ammonium-selective membrane, then a biosensor for measuring urea concentrations is produced. Both membranes 22 and 23 can be introduced successively into the opening 16 as discussed above from liquid phase, and solidified. The reference electrode is configured in the same way as in the second illustrative embodiment (FIG. 4).

Figure 6:
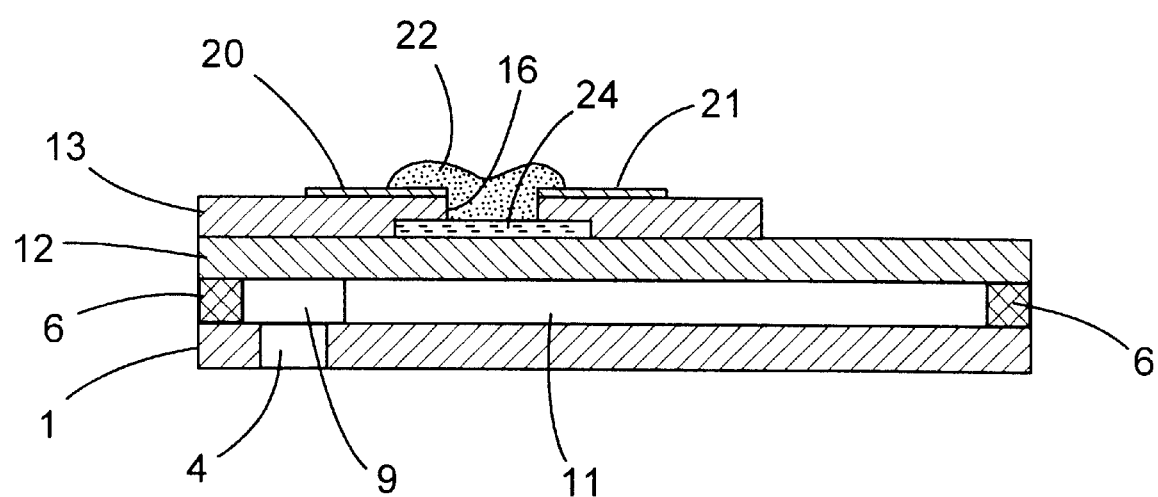
FIG. 6 shows a fourth illustrative embodiment of a sampling system with a sensor element for measuring gases dissolved in liquids.

The fourth illustrative embodiment (FIG. 6) shows a sensor element for measuring dissolved gases in liquids. It is constructed in a way similar to that represented in FIG. 4. However, here in FIG. 6, an additional gas-permeable membrane 24 is incorporated by lamination between the membrane 12 and the cover 13. This gas-permeable membrane is, for example, made of a 50 μm thick PTFE film. In order to configure an oxygen sensor of the Clark type, the noble-metal films 20, 21 are not, in contrast to the preceding illustrative embodiments, made of the same material and are not connected to one another. The noble-metal film 20 is, for example, made of platinum (cathode) and the noble-metal film 21 is made of silver whose surface is chloridized (Ag/AgCl anode). The membrane 22 is designed as a KCl gel. The oxygen can diffuse, through the dialysis membrane 12 and the gas-permeable membrane 24, to the platinum cathode where it undergoes electrochemical reaction and an electric current flows between the Pt cathode 20 and the Ag/AgCl anode 21, as is known in the case of Clark oxygen sensors.

Figure 7:
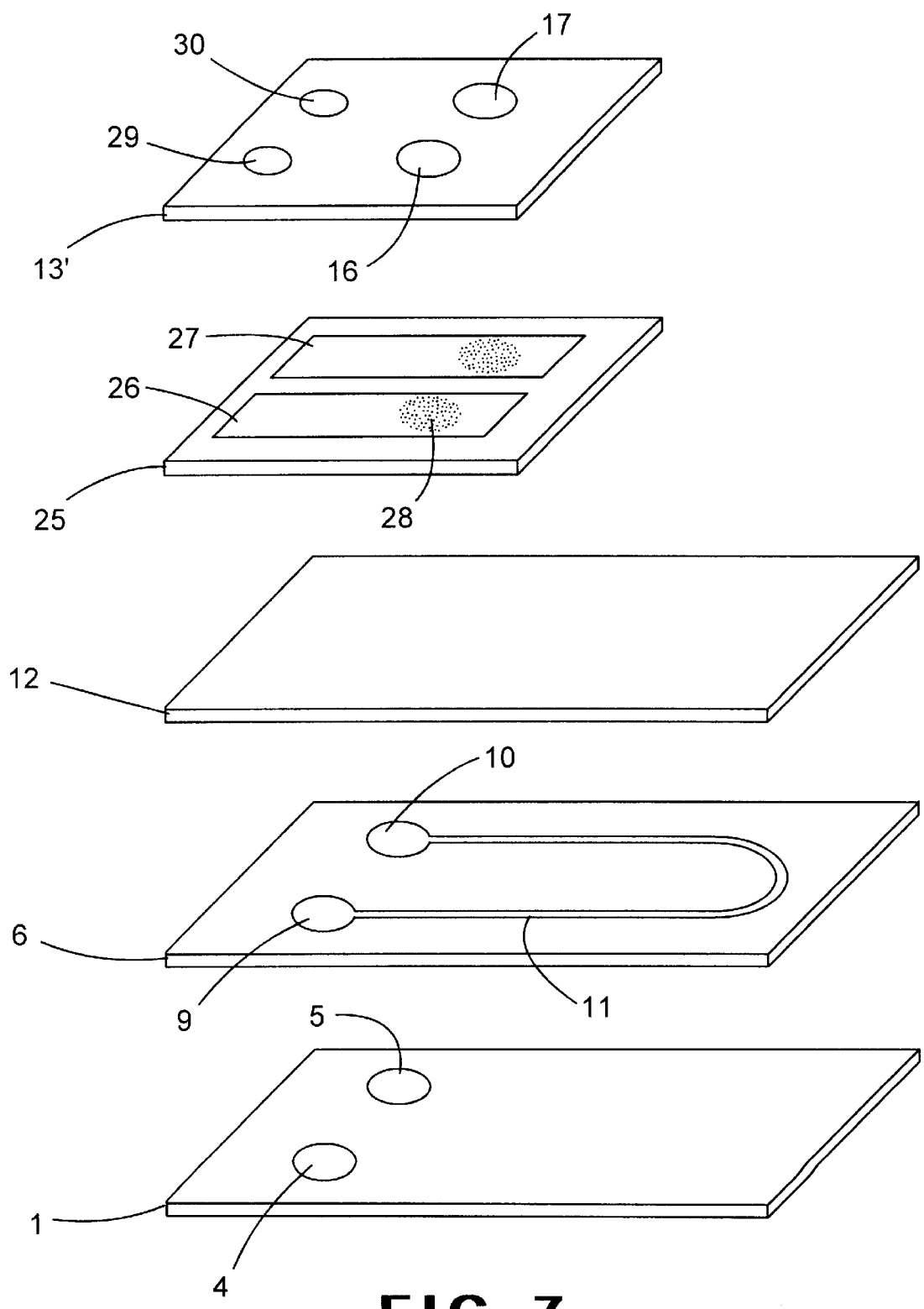
FIG. 7 shows a fifth illustrative embodiment of a sampling system with a glucose sensor.
Figure 8:
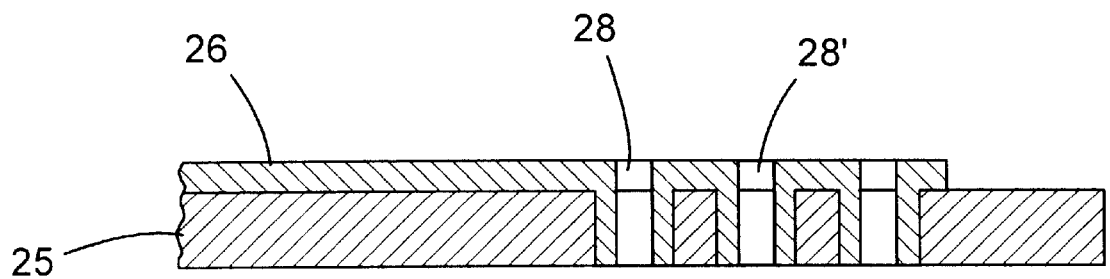
FIG. 8 shows a third illustrative embodiment of a sampling system with a biosensor element.
Figure 9:
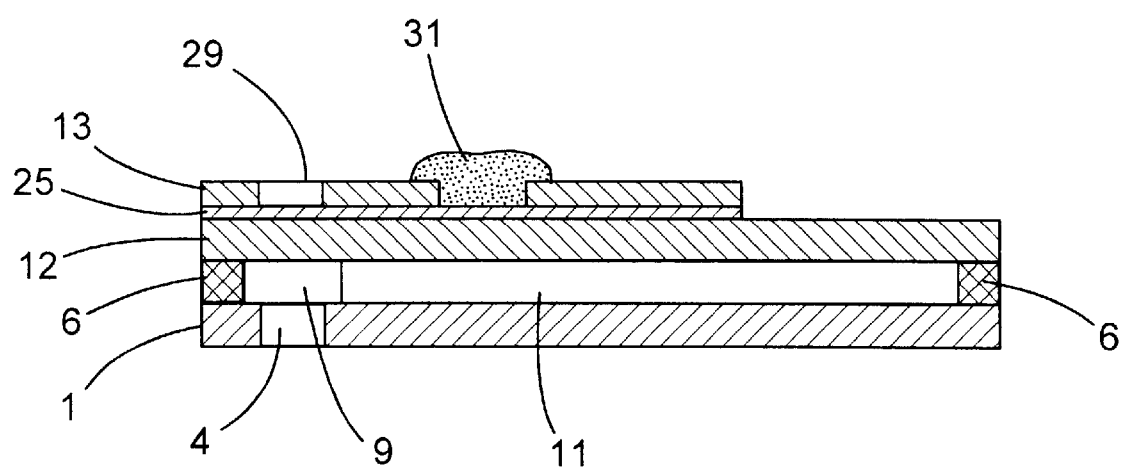
FIG. 9 shows a sampling system according to FIG. 7 with a glucose sensor.

A fifth illustrative embodiment (FIGS. 7 to 9) represents a glucose sensor. FIG. 7 shows a layer sequence according to FIG. 1. In addition, here in FIG. 7, there is an electrode support 25 made of the same material as the support 1 and the channel support 6. The electrode support 25 is coated with a platinum layer 26 and a silver film 27 with the aid of the methods mentioned above. Both films 26, 27 have layer thicknesses of between 0.1 and 1 μm. During operation of the sensor element, the surface of the silver film 27 is converted into silver chloride. The electrode body 25 with the noble-metal film 26 is represented in FIG. 8 on an enlarged scale in section. The electrode body is provided with small orifices 28 whose diameters are between 50 and 1000 μm. FIG. 9 shows the configuration once assembled, likewise in section. The gel layer 31 is, for example, made of polyvinyl alcohol (PVA) and is introduced by filling the opening 16 in the support 13 with a solution and solidified, as is known from DE 44 08 352. The enzyme glucose oxidase is immobilized in it.

In order to produce a reference electrode, the opening 17 is filled with a KCl gel.

In order to measure the glucose concentration, an electric voltage (typically 600 mV) is applied with the aid of two contact pins through the holes 29, 30 in the cover 13 between the Pt electrode 26 and the Ag/AgCl electrode 27 to the electrode support 25, and an electric current depending on the glucose concentration is measured.

It is, however, also possible to form the electrode body 25 such that the orifices 28 are not introduced until the metal layers 26, 27 have been applied, so that the inner walls of the orifices 28 are not metal-coated. This is important if potentiometric instead of amperometric sensor elements are produced using electrode bodies 25 of this type.

Figure 10:
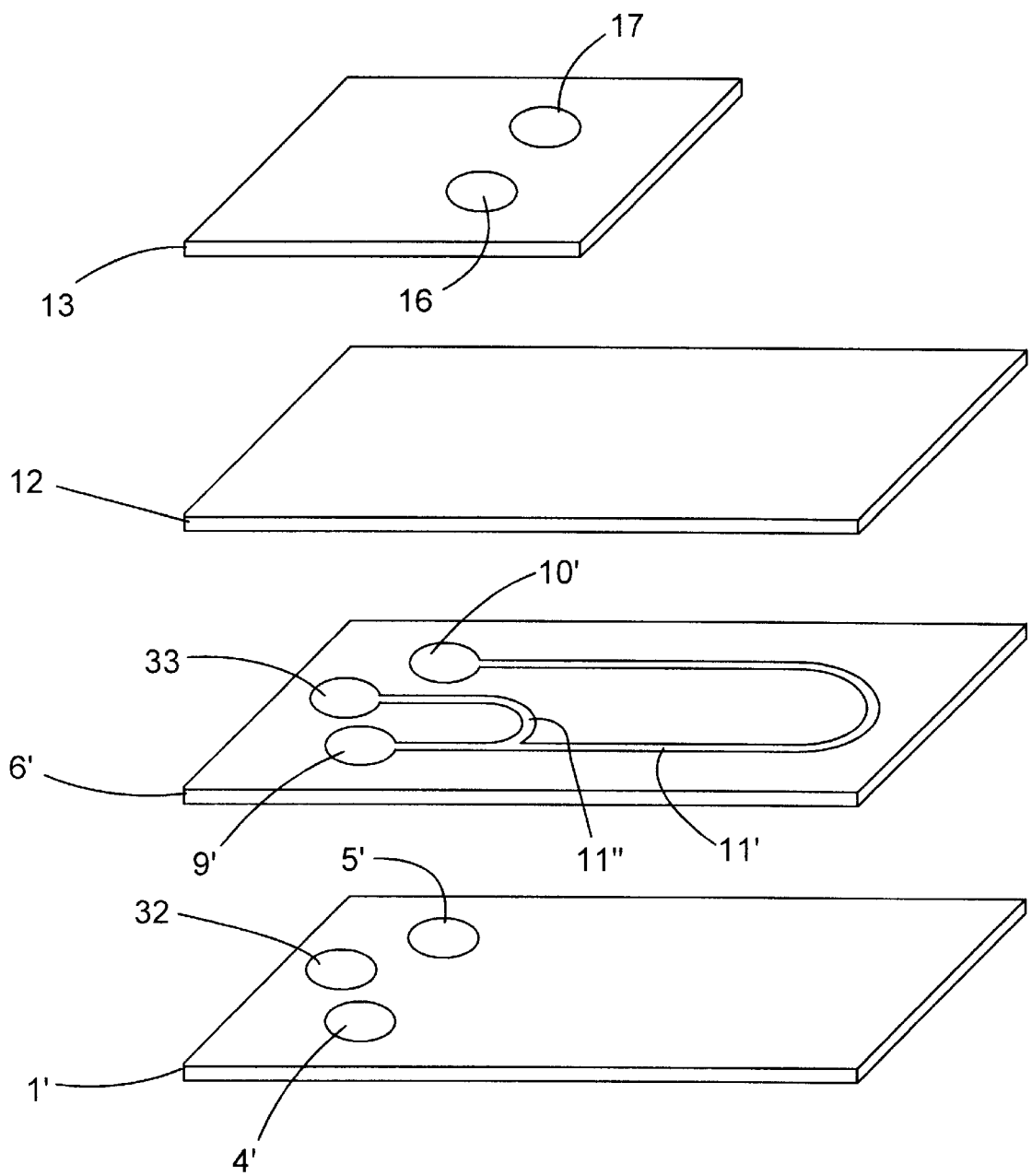
FIG. 10 shows a sampling system of a sixth illustrative embodiment with an additional end to the channel.

A sixth illustrative embodiment is represented in FIG. 10. This configuration corresponds to the representation in FIG. 1. However, in this case, an additional channel 11" is introduced into the channel support 6'. A calibration liquid can be fed through the holes 32 and 33 to the sensor element located in the opening 16.

Figure 11:
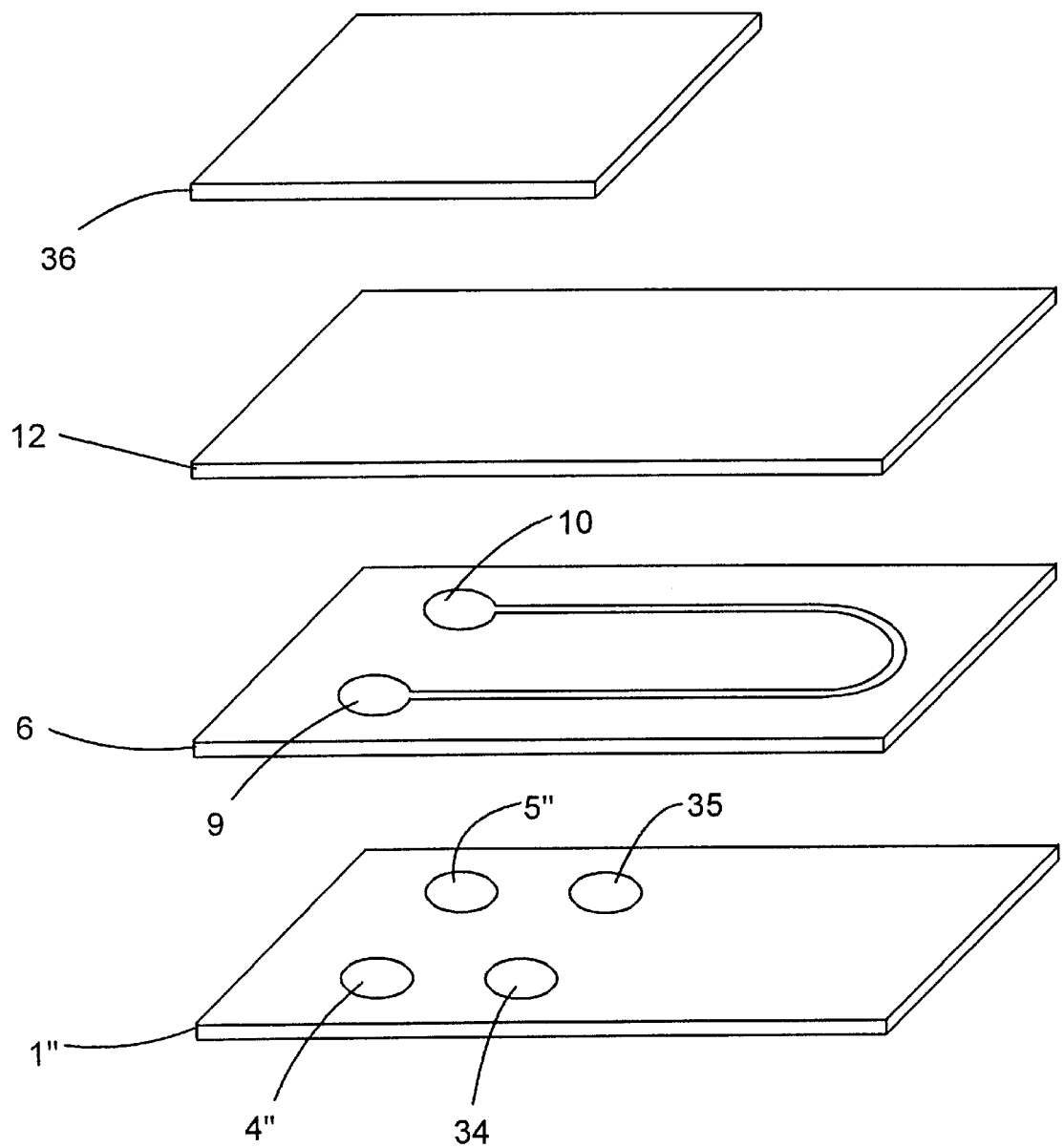
FIG. 11 shows a seventh illustrative embodiment of a sampling system.

FIG. 11 represents a seventh illustrative embodiment based on FIG. 1. In this case, however, the openings 16, 17 in the cover 13 (FIG. 1) are replaced by the openings 34, 35 which are located in the support 1". As shown in the illustrative embodiment 2, a sensor element according to FIG. 3 and a reference electrode are inserted into these openings.

Figure 12:
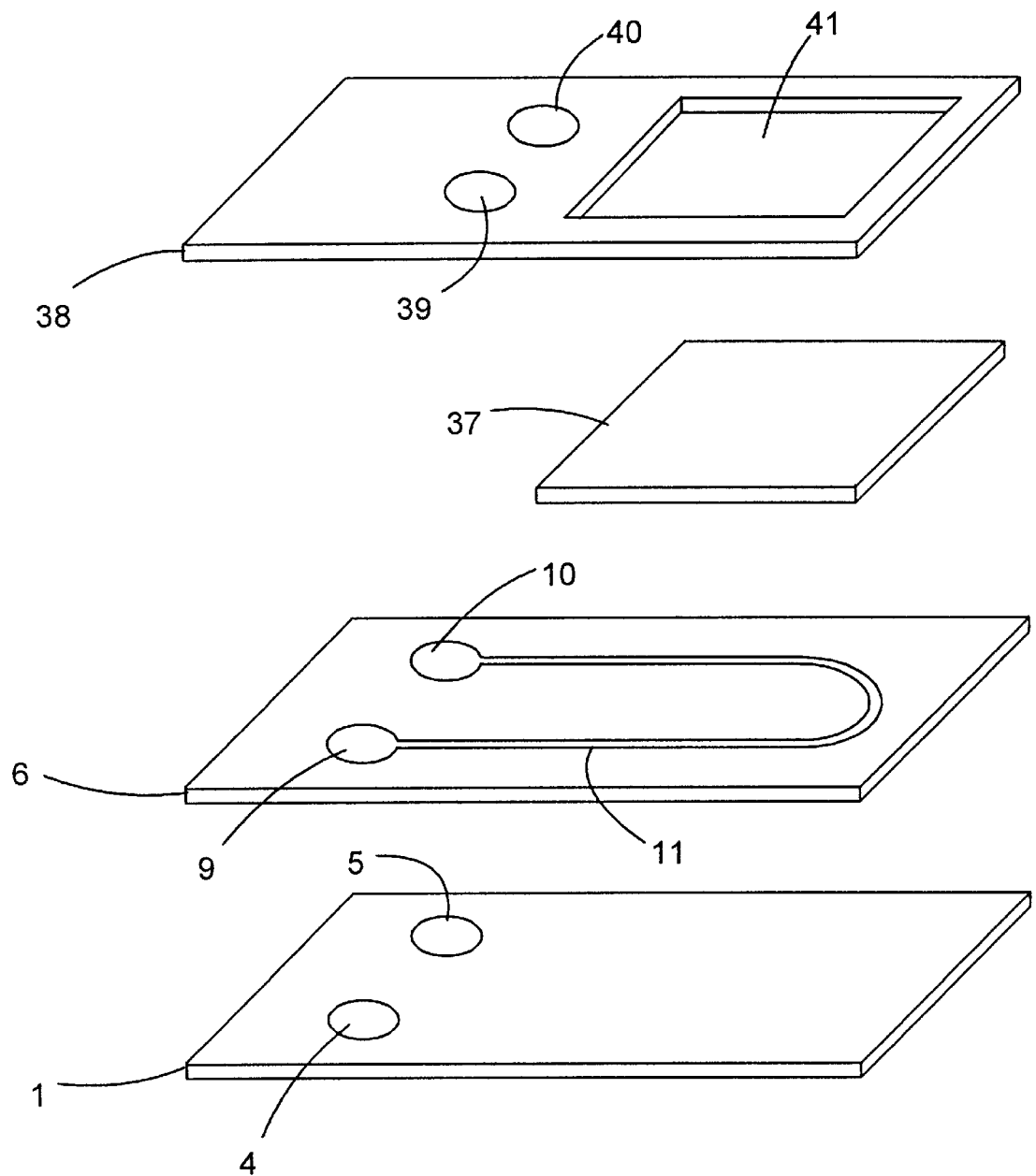
FIG. 12 shows a sampling system according to an eighth illustrative embodiment.

FIG. 12 shows an eighth illustrative embodiment on the basis of FIG. 1. In this case, the membrane 37 (this replaces the membrane 12) only partly covers the channel support 6. The cover 38 is of a larger design and has a window 41, through which the medium to be measured can be brought into contact with the membrane 37. As described above, sensor elements and reference electrodes can be produced in the openings 39, 40.

Figure 13:
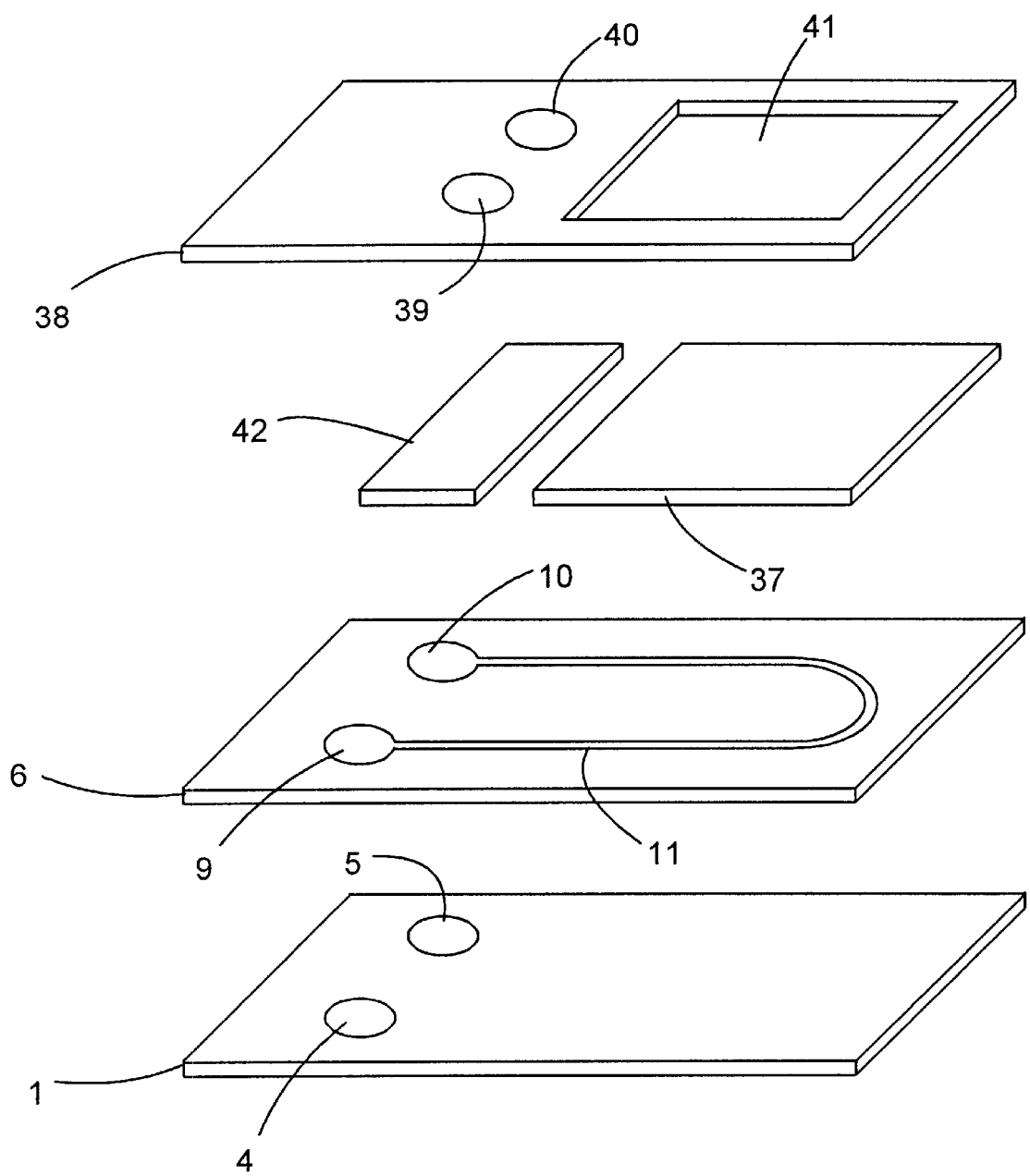
FIG. 13 shows a sampling system of a ninth illustrative embodiment with an additional membrane.

FIG. 13 represents a ninth illustrative embodiment. In addition to a dialysis membrane 37 (cf. FIG. 12 also), a gas-permeable further membrane 42 (for example made of PTFE) is in this case introduced. A sensor for dissolved oxygen can be produced in the opening 39 in similar fashion to the fourth illustrative embodiment.

Tenth illustrative embodiment: it is also possible to produce the membrane 42 in FIG. 13 using a thin PVC sheet, and to fill the openings 39, 40 with a solution for creating an ion-selective PVC membrane, and therefore to form an ion-selective sensor element in similar fashion to illustrative embodiment two.

Figure 14:
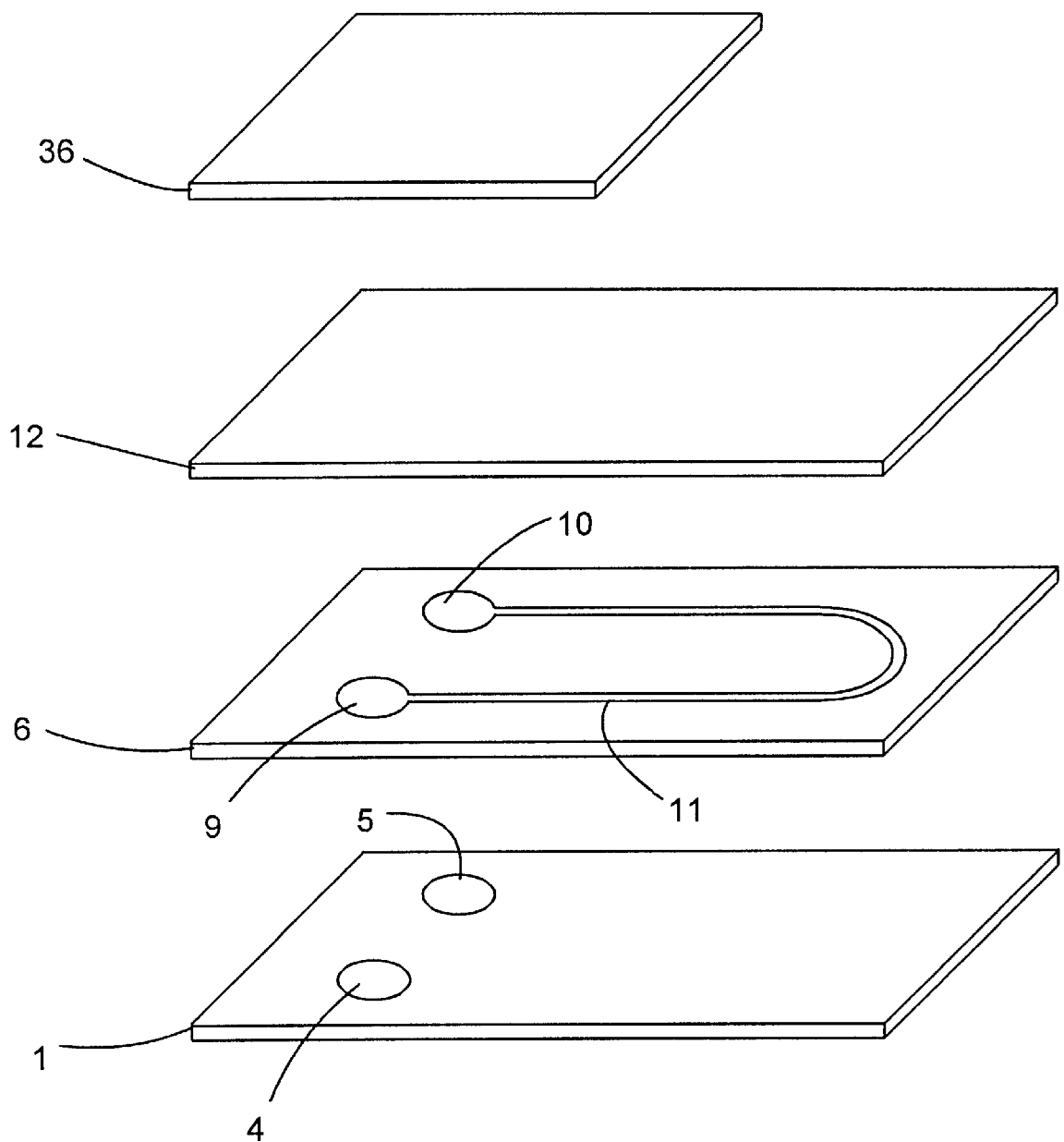
FIG. 14 shows a sampling system in an eleventh illustrative embodiment with external connection of sensor elements.

FIG. 14 shows an eleventh illustrative embodiment. In contrast to the first illustrative embodiment, no sensor elements and reference electrodes are in this case produced in openings in the cover (13 in FIG. 1, 36 in FIG. 14). This device is used as a sampling unit based on the microdialysis principle. Sensors can be introduced externally into the liquid flow which flows through the channel 11.

In a twelfth illustrative embodiment (FIG. 15), in contrast to FIG. 1, the support and the channel support (1 and 6 in FIG. 1) are combined to form one unit 43. This support 43 is, for example, made of PVC and is 5 mm thick. The holes 44, 45 extend over the entire thickness; the channel 46 has a depth of 1 mm.

Figure 15:
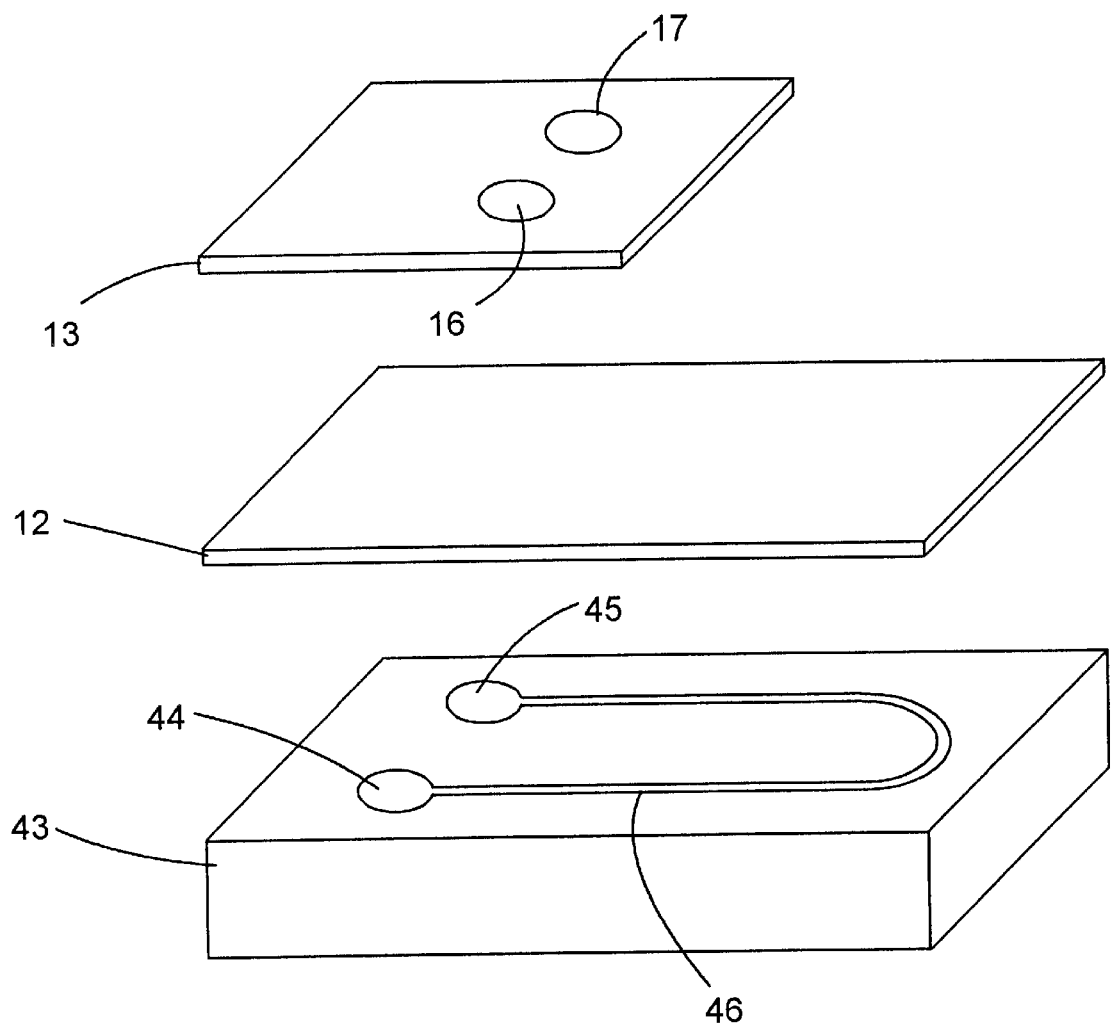
FIG. 15 shows a sampling system in a twelfth illustrative embodiment.
Figure 16:
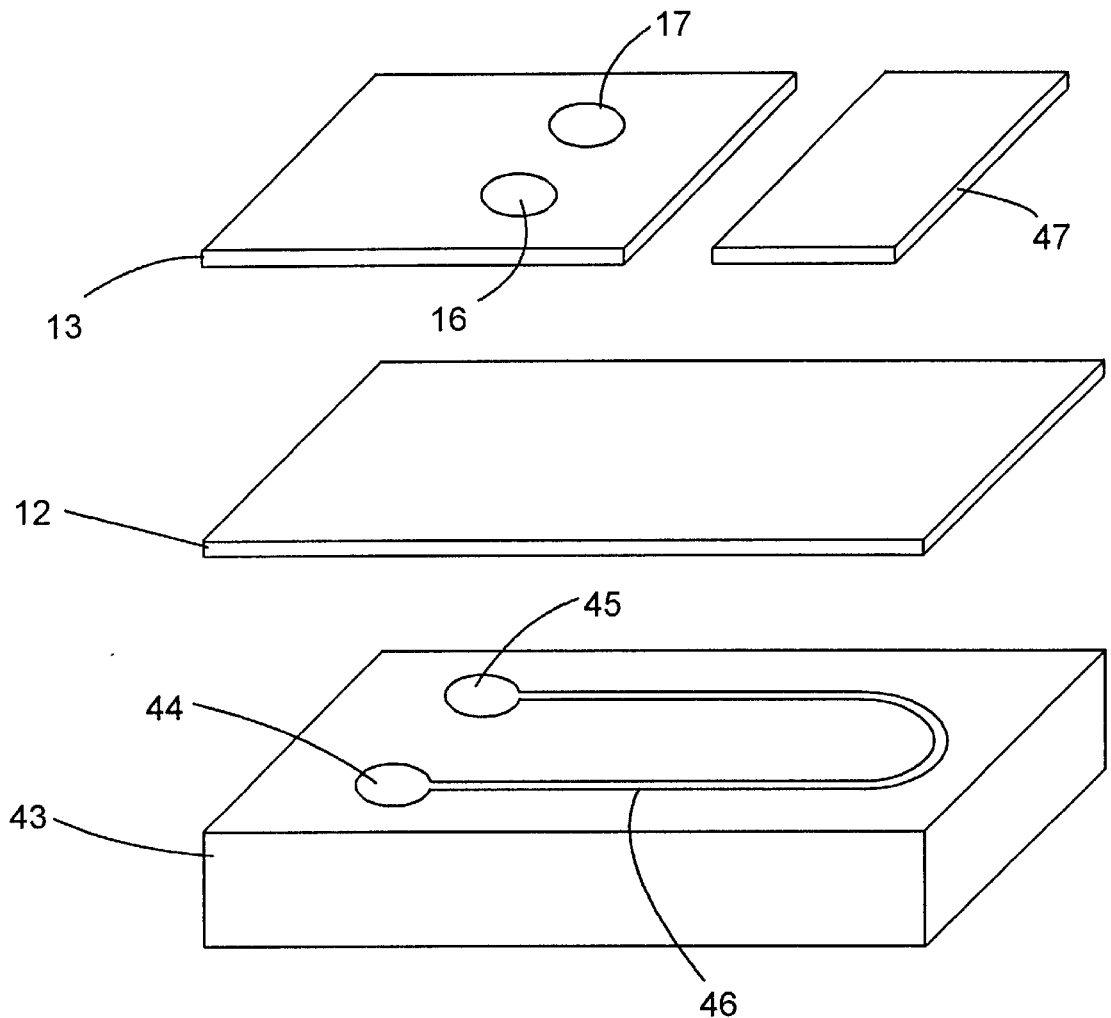
FIG. 16 shows a sampling system in a thirteenth illustrative embodiment.

In FIG. 16, the thirteenth illustrative embodiment shows a configuration according to FIG. 15. In this case, a sampling layer 47 is additionally bonded adhesively to the membrane 12. This layer 47 is made of filter paper, which can take up a drop of the liquid medium.

Figure 17:
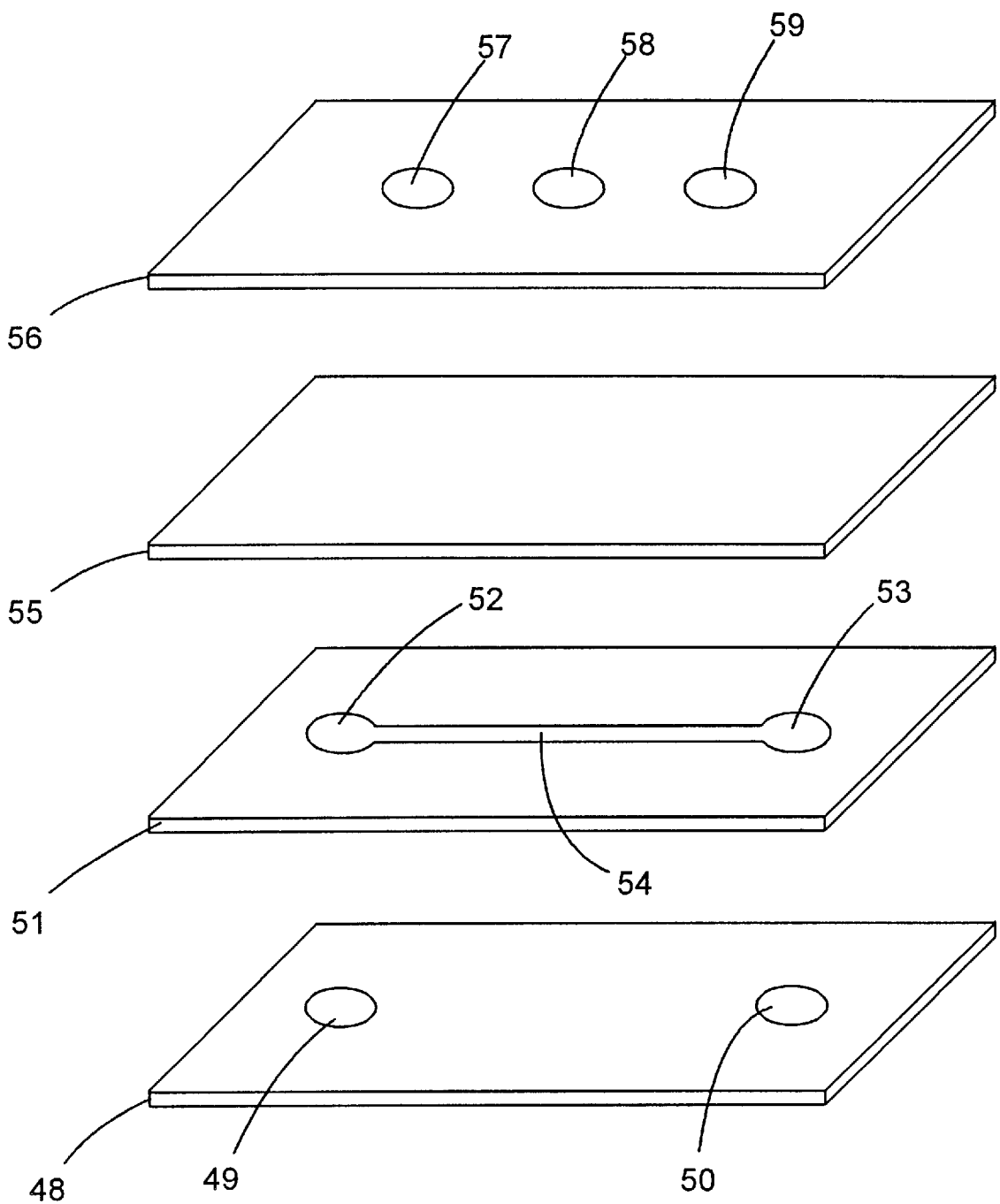
FIG. 17 shows a sampling system in a fourteenth illustrative embodiment, into which sensor elements can be integrated.

FIG. 17 shows a fourteenth illustrative embodiment. A continuous-flow arrangement is represented, which is made up of a support 48, a channel support 51, a membrane 55 (dialysis membrane or gas-permeable membrane) as well as a cover 56 in whose openings 57, 58, 59 it is possible to introduce sensor elements and reference electrodes, as mentioned above. The arrangement operates in the manner of a sensor continuous-flow cell to which the liquid medium to be measured is fed through the hole 49 and then removed through the hole 50.

Figure 18:
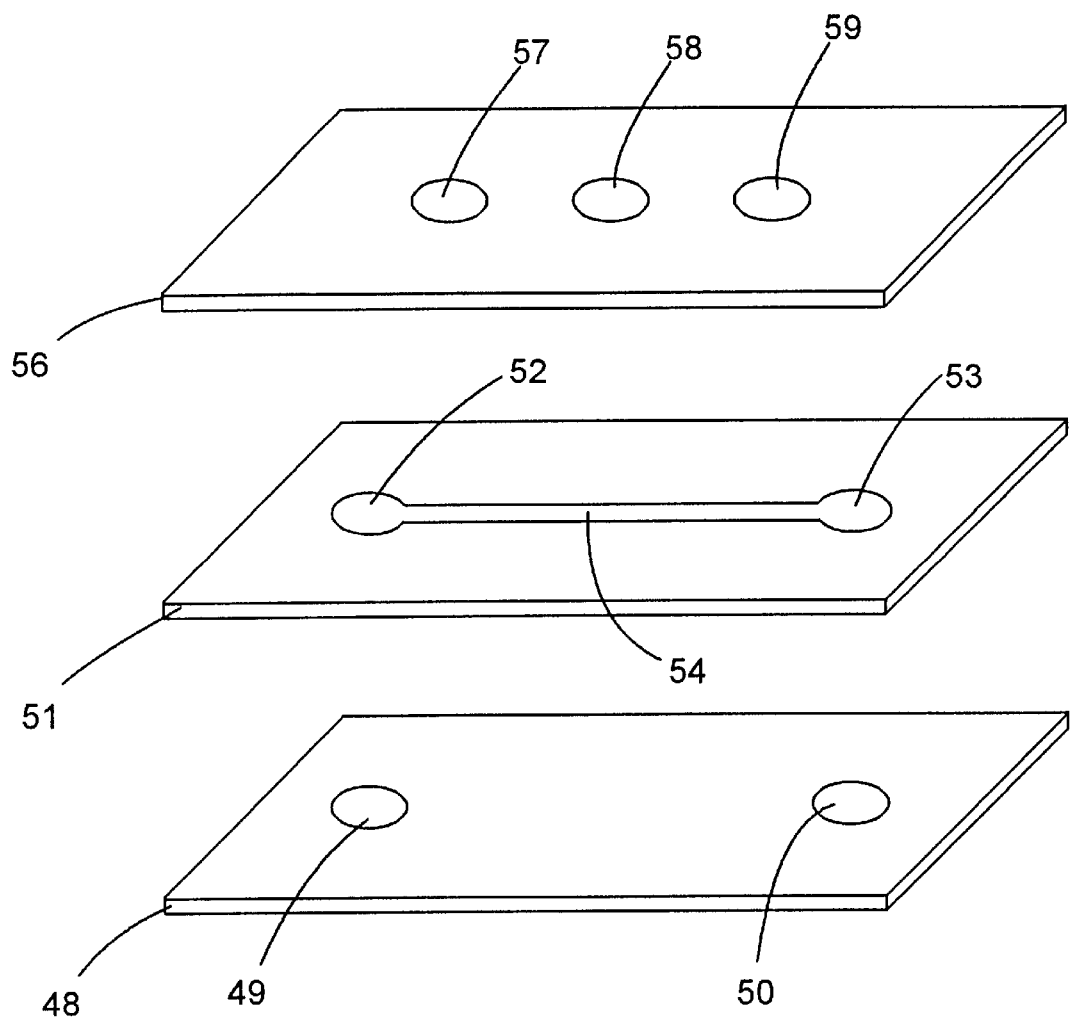
FIG. 18 shows a sampling system as a fifteenth illustrative embodiment, into which sensor elements can be integrated.

FIG. 18 shows a fifteenth illustrative embodiment on the basis of FIG. 17. However, the membrane 55 is omitted in FIG. 18. Sensor elements according to FIG. 3 may be inserted into the openings 57, 58, 59.

Figure 19:
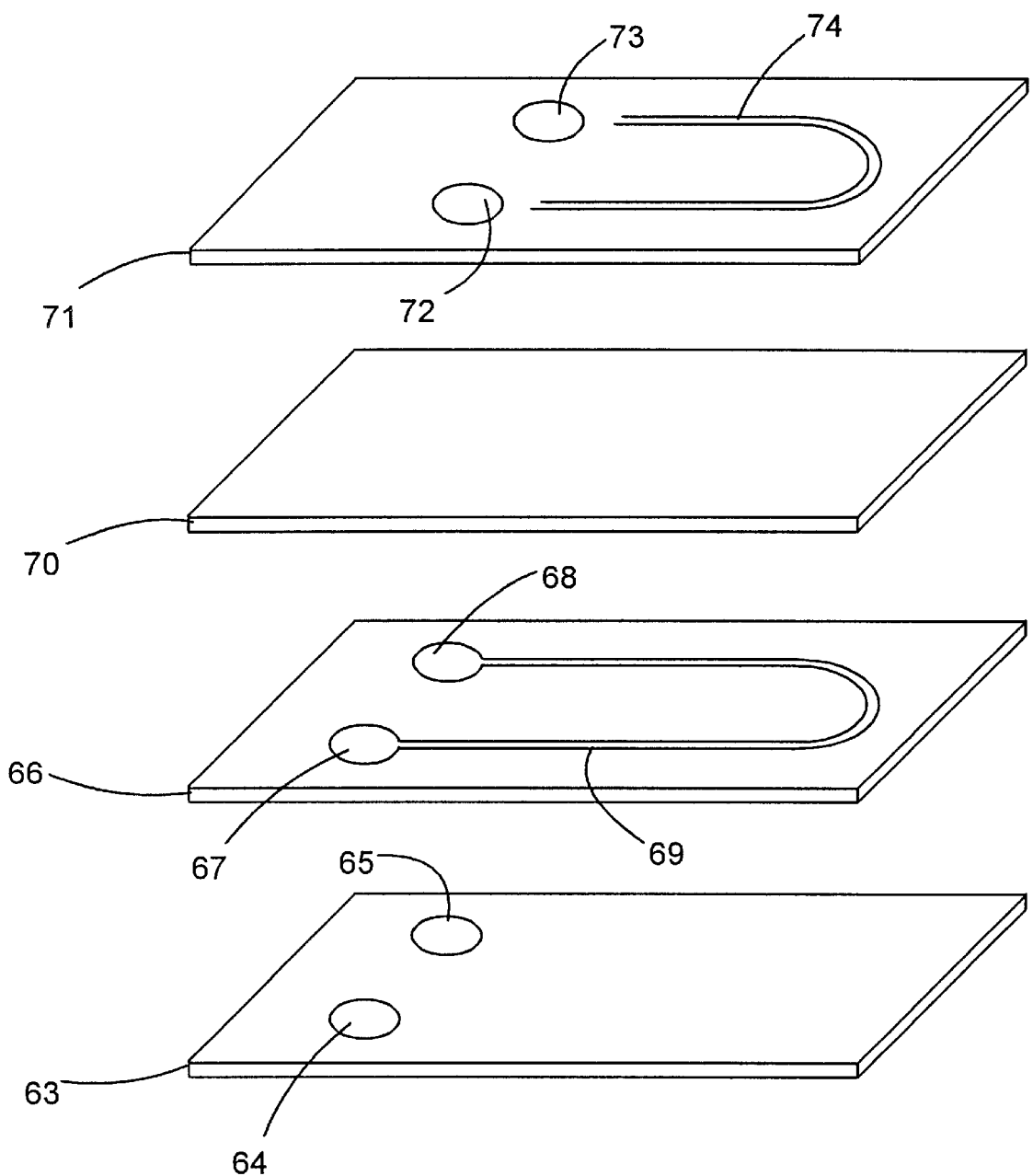
FIG. 19 shows a sampling system in a sixteenth illustrative embodiment with an integrated reaction section.

FIG. 19 represents a sixteenth illustrative embodiment as a layer sequence. All the layers are again firmly connected to one another.

In this case, a liquid medium to be measured is fed through the hole 64 in the support 63 to the channel 69, and then removed through the hole 65. The medium to be measured flows through the channel 69 in the channel support 66. Through the dialysis membrane 70, the liquid medium to be measured is in contact with a reactive material which is introduced into the channel-shaped hole (reaction section 74) in the cover 71. Sensor elements and reference electrodes, which measure the concentration of substances before and after the reaction section, are again introduced in the openings 72, 73.

A polymer, gel or hydrogel with immobilized enzymes, antibodies or microorganisms can be used as reactive material. If, for example, oxygen-metabolizing microorganisms are contained in the reaction section and the sensor elements in the openings 72, 73 are formed as oxygen sensors, then a sensor system for biological oxygen demand can be produced.

FIG. 20 shows an arrangement according to FIG. 4. In this case, the carrier liquid is supplied and discharged by means of a plastic block 76 having at least one channel 77 which is made tight against the support 1 with the aid of an O-ring 78. In addition to FIG. 4, the membrane material 22 is sealed with an epoxy resin encapsulation layer 75.

Figure 21:
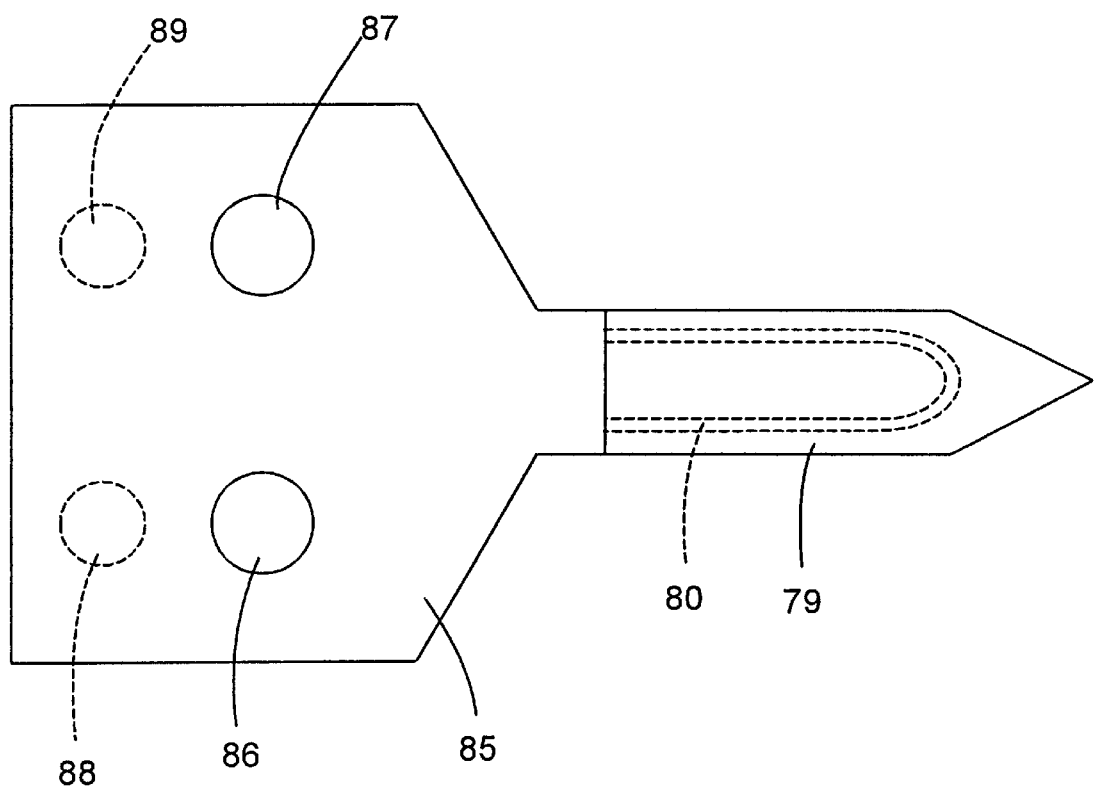
FIG. 21 shows a needle-shaped sampling and sensor unit.

FIG. 21 shows an arrangement according to FIG. 2, which is formed with a needle shape at the tip. The width of the needle probe is from 0.1 to 5 mm. The channel 80 in the channel support can be seen under the membrane 79. As mentioned above, sensor elements and reference electrodes are inserted in the openings 86, 87 in the cover 85. The carrier liquid can be fed and discharged through the holes 88, 89. This needle-shaped design is suitable, for example, for insertion into tissue.

Figure 22:
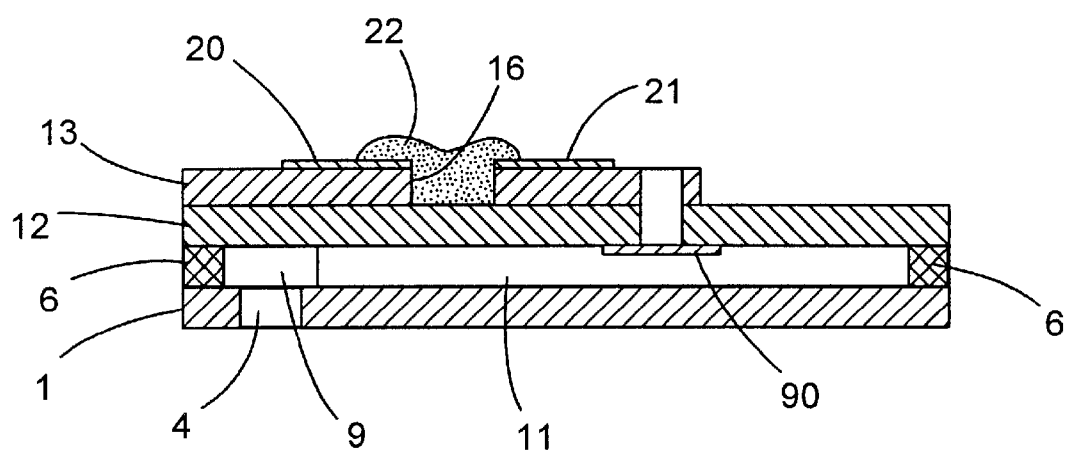
FIG. 22 shows a sampling system in a further illustrative embodiment.

FIG. 22 represents a further illustrative embodiment of a sampling system formed according to the invention. In this case, the essential structure corresponds to the example explained above in the description of FIG. 4. At least one electrode 90 has in this case additionally been arranged in the channel 11, in order to achieve an electrochemical reaction therein.

The electrode(s) 90 may, for example, be applied using a known thin-film or screen printing method.

Besides this, however, there is a further possibility (not shown in FIG. 22) of arranging the electrode(s) on the opposite side of the membrane 12 from the channel 11. These electrode(s) may, for example, be applied in the form of metallic paste.

By virtue of the electrochemical reaction that may be obtained in this way, a further improvement can be obtained in the isolation of the analytes to be determined.

What is claimed is:

1. Sampling system for fluid analytes or analytes contained in fluids, having a flat support and a channel support comprising a channel through which fluid can be fed via holes in the support, the channel being at least partly covered by a cover, characterized in that a membrane which is permeable to the analyte is arranged between the cover and the open upper side of the channel in such a way that it at least partly covers this channel, and the analyte can be taken from or measured at regions which are not closed by the cove.

2. Sampling system according to claim 1, characterized in that the channel is formed in a channel support, which is connected to the flat support.

3. Sampling system according to claim 1, characterized in that holes are formed in the channel support to correspond to holes formed in the flat support.

4. Sampling system according to claim 1 characterized in that the flat support, the channel support and/or the cover are made of plastic (polyvinyl chloride (PVC), polyethylene (PE), polyoxymethylene (POM), polycarbonate (PC), ethylene/propylene copolymer (EPDM), polyvinylidene chloride (PVDC), polychlorotrifluoroethylene, polyvinyl butyral (PVB), cellulose acetate (CA), polypropylene (PP), polymethyl methacrylate (PMMA), polyamide (PA), tetrafluoroethylene/hexafluoropropylene copolymer (FEP), polytetrafluoroethylene (PTFE), phenol formaldehyde (PF), epoxide (EP), polyurethane (PUR), polyester (UP), silicone, melamine formaldehyde (MF), urea formaldehyde (UF), aniline formaldehyde, capton etc.) or of glass, ceramic or silicon.

5. Sampling system according to claim 1, characterized in that the flat support is formed with a length of from 1 to 10 cm, a width of from 0.5 to 5 cm and a thickness of from 0.1 to 1 mm, and the channel support has approximately the same size, the holes have a diameter of between 0.1 and 10 mm, and the width of the channel is between 0.1 and 10 mm.

6. Sampling system according to claim 1, characterized in that the membrane is formed as a dialysis membrane or gas-permeable membrane, and its thickness is between 10 and 1000 $\mu$m.

7. Sampling system according to claim 6, characterized in that the dialysis membranes are made of materials selected from the group consisting of polycarbonate, cellulose acetate, cellulose hydrate, cuprophane, thomapor, regenerated cellulose, polyacrylonitrile, polysulphone, polyamide and polymethyl methacrylate.

8. Sampling system according to claim 6, characterized in that the gas-permeable membrane is made of materials selected from the group consisting of polyvinyl chloride (PVC), polyethylene (PE), polyoxymethylene (POM), polycarbonate (PC), ethylene/propylene copolymer (EPDM), polyvinylidene chloride (PVDC), polychlorotrifluoroethylene, polyvinyl butyral (PVB), cellulose acetate (CA), polypropylene (PP), polymethyl methacrylate (PMMA), polyamide (PA), tetrafluoroethylene/hexafluoropropylene copolymer (FEP), polytetrafluoroethylene (PTFE), phenol formaldehyde (PF), epoxide (EP), polyurethane (PUR), polyester (UP), silicone, melamine formaldehyde (MF), urea formaldehyde (UF), aniline formaldehyde and capton.

9. Sampling system according to claim 1, characterized in that at least one sensor element can be inserted into an opening which is formed as an uncovered region of the cover.

10. Sampling system according to claim 9, characterized in that the sensor element can be inserted in such a way that the ion-selective membrane of the sensor element is in direct contact with the membrane, and a noble-metal lead can be connected through the opening to measuring electronics.

11. Sampling system according to claim 9, characterized in that a hydrogel film is formed between the membrane of claim 1 and the ion-selective membrane of the sensor element as set forth in claim 10.

12. Sampling system according to claim 1, characterized in that a reference electrode is used with the system, said electrode constructed of a membrane layer of solidified KCl gel that, upon insertion of the electrode into an opening in the cover of the sampling system, comes into contact with the membrane layer of the sampling system, and that is fixedly-connected to a layer of a chloridized silver film having the same shape as the opening in the cover such that it may be inserted through the opening from the underside of the cover.

13. Sampling system according to claim 1, characterized in that optical sensor elements can be inserted into the openings.

14. Sampling system according to claim 1, characterized in that a 0.1 to 1 $\mu$m thick chloridized silver film is applied to the cover by means of evaporation, sputtering or screen printing techniques, and a membrane solution made of PVC or silicone with ion carriers is introduced into one opening in the cover, and a separate membrane solution of KCl gel is introduced into a second opening in the cover to form a reference electrode.

15. Sampling system according to claim 1, characterized in that an additional membrane is introduced, this membrane is designed as a gel layer with an enzyme and the membrane of claim 1 is formed as a pH-sensitive or ammonium-selective membrane.

16. Sampling system according to claim 1, characterized in that a gas-permeable membrane comprised of a 20 to 100 $\mu$m thick PTFE film is arranged at the sensor element, between the membrane of claim 1, which is designed as a KCl gel, and the cover and two noble-metal films, one made of platinum (cathode) and one made of chloridized silver (Ag/AgCl anode), are applied to the cover.

17. Sampling system according to claim 1, characterized in that an electrode support is interposed between the membrane of claim 1 and the cover, said electrode support having a platinum film and a chloridized silver film both between 0.1 and 1 $\mu$m thick and having multiple small orifices whose diameters are between 50 and 1000 $\mu$m at one end, said films fixedly-connected to the upper side of the electrode support such that the small orifices of the platinum film correspond with one opening in the cover through which a gel layer of polyvinyl alcohol (PVA) having the enzyme glucose oxidase immobilized in it is introduced and solidified, and the small orifices of the chloridized silver film correspond with a separate opening in the cover that is filled with a KCl gel.

18. Sampling system according to claim 17, characterized in that the electrode body is formed in such a way that the inner walls of the orifices are not metal-coated.

19. Sampling system according to claim 1, characterized in that an additional channel is introduced into the channel support, and a calibration liquid can be fed through a hole in the flat support which corresponds with a hole formed in the channel support and that is part of the channel to disperse through the membrane layer to a sensor element which is inserted into an opening in the cover.

20. Sampling system according to claim 1, characterized in that openings, into which a sensor element and a reference electrode can be inserted, are formed in the support.

21. Sampling system according to claim 1, characterized in that the membrane can be inserted, in such a way that it can partly cover the channel, into a window in the cover, and sensor elements and reference electrodes can be inserted in openings in the cover.

22. Sampling system according to claim 1, characterized in that a dialysis membrane and a gas-permeable membrane are introduced and a sensor for dissolved oxygen is inserted in an opening in the cover.

23. Sampling system according to claim 1, characterized in that the membrane is made of a thin PVC sheet and two openings in the cover are filled with a solution for creating an ion-selective PVC membrane, and an ion-selective sensor element is therefore formed.

24. Sampling system according to claim 1, characterized in that the flat support of claim 1 and channel support of claim 1 are formed as a unit having two holes extending through the entire thickness of the unit comprising the support and channel support, and are connected by a 1 mm deep channel formed on the upper side of the channel support.

25. Sampling system according to claim 1, characterized in that a layer for taking up the sample is additionally applied to the membrane, and this layer (47) is made of filter paper.

26. Sampling system according to claim 1, characterized in that a flat support having two openings is fixedly connected to the bottom side of a separate and distinct channel support that has two openings connected by a channel on its upperside and is fixedly connected to a membrane, said membrane being fixedly connected to a cover having three openings in which sensor elements and reference electrodes can be inserted, the flat support and channel support arranged such that a fluid carrying a given analyte can be supplied through one of the openings in the flat support, flow through the opening in the channel support to the channel and then through the channel to disperse the analyte in the membrane for analysis, and the carrier fluid may be discharged through the other opening in the channel support and flat support.

27. Sampling system according to claim 26, characterized in that the opening in the flat support that corresponds with the opening in the channel support is formed with a needle shape to accommodate a needle probe from 0.1 to 5 mm wide.

28. Sampling system according to claim 1, characterized in that a channel-shaped hole containing a reactive material is introduced as a reaction section in the cover, and sensor elements and reference electrodes, for measuring the concentration of substances before and after the reaction section, are introduced in the openings.

29. Sampling system according to claim 1, characterized in that the carrier liquid is supplied and discharged by means of a plastic block having at least one channel which is made tight against the support with the aid of an O-ring, and the membrane material is additionally sealed with an epoxy resin encapsulation layer.

30. Sampling system according to claim 1, characterized in that at least one electrode which causes electrochemical reactions is arranged in the channel or above the membrane which is permeable to the analyte.

31. Process for producing a sampling system according to claim 1, characterized in that the holes in the flat support, the channel support, and the cover, as well as the channel grooves are produced by injection-moulding or compression techniques or the LIGA method during the manufacture of the support the cover and/or the channel support, or characterized in that the holes in the flat support, channel support and cover are produced subsequent to the assembly of the sampling system by cutting, stamping, milling, boring, etching, laser cutting or electric discharge machining.

32. Process according to claim 31, characterized in that a sensor element is produced by applying a 0.1 to 1 $\mu$m thick noble-metal film of chloridized silver to the cover by means of the evaporation, sputtering or screen printing techniques, and introducing a membrane solution of KCl gel into an opening in the cover with the aid of a micropipette or an automatic dispenser, and subsequently solidifying the KCl gel by evaporating the solvent or by cross-linking under UV light, and a separate element is similarly introduced into a second opening in the same cover to produce a reference electrode.

33. Process according to claim 32, characterized in that a chloridized silver film is applied to the cover, and PVC or silicone with ion carriers is introduced into one opening in the cover, forming an ion-selective sensor element, and a KCl gel is introduced into a second opening in the cover to form a reference electrode.

34. Process according to claim 31, characterized in that the support, the charmel support, the cover and the membrane are connected to form the sampling system, by welding or hot-laminating with laminating sheets or adhesive bonding or anodic bonding.

35. Process according to claim 31, characterized in that the support, the channel support and the cover are made from a 150 $\mu$m thick laminating sheet by stamping, this sheet is made of polyethylene or polyester, furthermore the membrane is a 50 $\mu$m thick polycarbonate dialysis membrane, and the solid connection of the support, the channel support, the membrane and/or the cover is made by laminating at 125° C.

* * * * *